(12) United States Patent
Joseph

(10) Patent No.: US 9,629,560 B2
(45) Date of Patent: Apr. 25, 2017

(54) IMPLANTABLE VITAL SIGN SENSOR

(71) Applicant: Thomas Jefferson University, Philadelphia, PA (US)

(72) Inventor: Jeffrey I Joseph, Penn Valley, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 15/083,729

(22) Filed: Mar. 29, 2016

(65) Prior Publication Data

US 2016/0287174 A1    Oct. 6, 2016

Related U.S. Application Data

(60) Provisional application No. 62/168,754, filed on May 30, 2015, provisional application No. 62/143,592, filed on Apr. 6, 2015.

(51) Int. Cl.
*A61B 5/02* (2006.01)
*A61B 5/0215* (2006.01)
(Continued)

(52) U.S. Cl.
CPC ............ *A61B 5/0215* (2013.01); *A61B 5/076* (2013.01); *A61B 5/14551* (2013.01); *A61B 5/686* (2013.01); *A61B 5/6876* (2013.01); *A61B 5/6879* (2013.01); *A61B 5/0031* (2013.01); *A61B 2562/0247* (2013.01)

(58) Field of Classification Search
CPC ....... A61B 5/686; A61B 5/076; A61B 5/0215; A61B 2562/0247
See application file for complete search history.

(56) References Cited

U.S. PATENT DOCUMENTS 3,049,001 A    8/1962    Mackay et al.
5,749,367 A    5/1998    Gamlyn et al.
(Continued)

FOREIGN PATENT DOCUMENTS

WO    9829030    7/1998
WO    2004014456 A2    2/2004
(Continued)

OTHER PUBLICATIONS

James Xin Sun, Cardiac Output Estimation using Arterial Blood Pressure Waveforms, Massachusetts Institute of Technology, Sep. 2006, 7 pages.
(Continued)

*Primary Examiner* — Tiffany Weston
(74) *Attorney, Agent, or Firm* — Christopher & Weisberg, P.A.

(57) ABSTRACT

An implantable vital sign sensor including a housing including a first portion, the first portion defining a first open end, a second open end opposite the first end, and a lumen there through, the first portion being sized to be implanted substantially entirely within the blood vessel wall of the patient. A sensor module configured to measure a blood vessel blood pressure waveform is included, the sensor module having a proximal portion and a distal portion, the distal portion being insertable within the lumen and the proximal portion extending outward from the first open end.

1 Claim, 5 Drawing Sheets

(51) Int. Cl.
 *A61B 5/1455* (2006.01)
 *A61B 5/07* (2006.01)
 *A61B 5/00* (2006.01)

(56) References Cited

U.S. PATENT DOCUMENTS

| | | | |
|---|---|---|---|
| 5,995,860 A | 11/1999 | Sun et al. | |
| 6,049,727 A | 4/2000 | Crothall | |
| 6,122,536 A | 9/2000 | Sun et al. | |
| 6,743,180 B1 | 6/2004 | Van Bockel | |
| 6,999,810 B2 | 2/2006 | Berner et al. | |
| 7,011,630 B2 | 3/2006 | Desai et al. | |
| 7,018,568 B2 | 3/2006 | Tierney | |
| 7,024,236 B2 | 4/2006 | Ford et al. | |
| 7,044,920 B2 | 5/2006 | Letort | |
| 7,150,975 B2 | 12/2006 | Tamada et al. | |
| 7,163,511 B2 | 1/2007 | Conn et al. | |
| 7,174,199 B2 | 2/2007 | Berner et al. | |
| 7,295,867 B2 | 11/2007 | Berner et al. | |
| 7,405,055 B2 | 7/2008 | Dunn et al. | |
| 7,450,999 B1* | 11/2008 | Karicherla | A61B 5/02152 607/126 |
| 7,519,478 B2 | 4/2009 | Bartkowiak et al. | |
| 7,521,019 B2 | 4/2009 | Polak et al. | |
| 7,523,004 B2 | 4/2009 | Bartkowiak et al. | |
| 7,604,593 B2 | 10/2009 | Parris et al. | |
| 7,647,831 B2 | 1/2010 | Corcoran et al. | |
| 7,699,775 B2 | 4/2010 | Desai et al. | |
| 7,711,493 B2 | 5/2010 | Bartkowiak et al. | |
| 7,731,867 B2 | 6/2010 | Li et al. | |
| 7,818,131 B2 | 10/2010 | Mott | |
| 7,873,399 B2 | 1/2011 | Berner et al. | |
| 7,935,499 B2 | 5/2011 | Dunn et al. | |
| 7,966,886 B2 | 6/2011 | Corcoran et al. | |
| 7,991,625 B2 | 8/2011 | Rosenfeld et al. | |
| 8,597,185 B2 | 12/2013 | Pipke | |
| 8,600,777 B2 | 12/2013 | Schoenberg et al. | |
| 8,602,999 B2 | 12/2013 | Young et al. | |
| 8,620,591 B2 | 12/2013 | Wegerich | |
| 2003/0069752 A1 | 4/2003 | LeDain et al. | |
| 2004/0152999 A1 | 8/2004 | Cohen et al. | |
| 2005/0288596 A1* | 12/2005 | Eigler | A61B 5/0215 600/485 |
| 2006/0178583 A1 | 8/2006 | Montegrande et al. | |
| 2007/0163353 A1 | 7/2007 | Lec et al. | |
| 2009/0093729 A1 | 4/2009 | Zhang et al. | |
| 2011/0124982 A1 | 5/2011 | Pipke | |
| 2011/0144967 A1 | 6/2011 | Adirovich | |
| 2013/0247644 A1 | 9/2013 | Swoboda et al. | |

FOREIGN PATENT DOCUMENTS

| | | | |
|---|---|---|---|
| WO | 2007010391 A1 | 1/2007 | |
| WO | 2013173747 A1 | 11/2013 | |

OTHER PUBLICATIONS

FDA Executive Summary, CardioMEMS Champion HF Monitoring System CardioMEMS, Inc., Prepared for the Oct. 9, 2013 meeting of the Circulatory Systems Devices Panel, P100045/A004, 52 pages.
Olive H. Murphy et al., Continuous in vivo blood pressure measurements using a fully implantable wireless SAW sensor, Biomed Microdevices (2013) 15:737-749, DOI 10.1007/s10544-013-9759-7.
Malcom Elliott and Alysia Coventry, Critical care: the eight vital signs of patient monitoring, British Journal of Nursing, 2012, vol. 21, No. 10, 5 pages.
Jay Ritzema et al., Direct Left Atrial Pressure Monitoring in Ambulatory Heart Failure Patients: Initial Experience With a New Permanent Implantable Device, Circulation. 2007;116:2952-2959; originally published online Dec. 3, 2007; doi: 101161/ CIRCULATIONAHA.107.702191.
H. Fassbender et al., Fully implantable blood pressure sensor for hypertonic patients, IEEE Sensors 2008 Conference, 4 pages.
Eric Y. Chow et al., Fully Wireless Implantable Cardiovascular Pressure Monitor Integrated with a Medical Stent, IEEE Transactions on Biomedical Engineering, vol. 57, No. 6. Jun. 2010, 10 pages.
P. Bingger et al., Highly Flexible capacitive strain gauge for continuous long-term blood pressure monitoring, Biomed Microdevices (2012) 14:573-581 DOI 10.1007/s10544-012-9636-9.
Marek Swoboda, Implantable Arterial Blood Pressure Sensor, A Thesis Submitted to the Faculty of Drexel University in partial fulfillment of the requirements for the degree of Doctor of Philosophy, Dec. 2004, 245 pages.
Faisal M. Merchant et al., Implantable Sensors for Heart Failure, Circulation Arrhythmia and Electrophysiology, 2010;3:657-667, doi: 10.1161/CIRCEP.110.959502.
Nader Najafi et al., MEMS implant for cardiovascular applications, MICRO NANO, the Newsletter of Tools adn Products in Micro and Nanotechnology, Sep. 2009, vol. 8, No. 9, 1 page.
LionsGate Technologies Inc., Mobile Vital Signs Monitoring: Everyone, Everywhere, A Technology Whitepaper by LionsGate Technologies Inc., Mar. 2013, 5 pages, info©LDTmedical.com, www.LGTmedical.com.
U. Kyriacos et al., Monitoring vital signs using early warning scoring systems: a review of the literature, Journal of Nursing Management, 2011, 19, 311-330.
Peng Cong et al., Novel Long-Term Implantable Blood Pressure Monitoring System with Reduced Baseline Drift, Proceedings of the 28th IEEE, EMBS Annual International Conference, New York City, USA, Aug. 30-Sep. 3, 2006, 4 pages.
Sim JJ., Overtreatment, undertreatment of hypertension raises risk for mortality and renal disease, Cardiology today, Am Coll Cardiol. 2014;64:588-59, Aug. 6, 2014.
MD+DI Staff, Promising Cardio Technologies, Heart disease kills one in four people in the United States, but these breakthrough technologies are aiming to change that, MedTechWorld, Jan. 2016, 6 pages.
Tia Gao, Vital Signs Monitoring and Patient Tracking Over a Wireless Network, Johns Hopkins University Applied Physics Laboratory, In Proceedings of the 27th Annual International Conference of the IEEE EMBS, Shanghai, Sep. 2005, 4 pages.
Ron Wilson, Watch for Small Warnings Before a Cardiac Arrest, Wall Street Journal, D1-D2, Tuesday, Feb. 2, 2016, 2 pages.
Dr. Mehran Mehregany, Wireless health to drive a trillion sensors, evaluationengineering.com, Mar. 2016, 3 pages.
John S. Ho et al., Wireless power transfer to deep tissue microimplants, 7974-7979, PNAS, Jun. 3, 2014, vol. 111, No. 22.
International Search Report and Written Opinion dated May 30, 2016 for International Application No. PCT/US2016/024655, International Filing Date Mar. 29, 2016 consisting of 14 pages.
Penc Cong et al.: "Wireless Batteryless Implantable Blood Pressure Monitoring Microsystem for Small Laboratory Animals", Article, Feb. 2010, vol. 10, No. 2, IEEE Sensors Journal, pp. 243-254, consisting of 12 pages.
Anna G.C.D. Ribeiro et al.: "Wireless Monitoring of Patient's Vital Signs", Laboratory of Hospital Automation and Bioengineering, Federal University of Rio Grande do Norte, State University of Rio Grande do Norte, Brazil, consisting of 21 pages.
Nuria Oliver et al.: "HealthGear: A Real-time Wearable System for Monitoring and Analyzing Physiological Signals", 2006 IEEE Computer Society, pp. 1-4, consisting of 4 pages.
Lawrence Yu et al., Chronically Implanted Pressure Sensors: Challenges and State of the Field, Sensors 2014, 14, 20620-20644; doi: 10.3390/s141120620. Received: Jun. 27, 2014; in revised form: Oct. 14, 2014 / Accepted: Oct. 21, 2014 / Published: Oct. 31, 2014, 25 pages.
Robert Tan et al., Development of a fully implantable wireless pressure monitoring system, Biomed Microdevices (2009) 11:259-264, DOI 10.1007/s10544-008-9232-1, Published online: Oct. 3, 2008, 6 pages.
Chih-Wen Cheng, et al., icuARM—An ICU Clinical Decision Support System Using Association Rule Mining, 10.1109/JTEHM.

(56) References Cited

OTHER PUBLICATIONS 2013.2290113, IEEE Journal of Transltional Engineering in Health and Medicine, Copyright (c) 2013, 10 pages.

Faisal M. Merchant et al., Implantable Sensors for Heart Failure, (Circ Arrhythm Electrophysiol. 2010;3:657-667), DOI: 10.1161/CIRCEP.110.959502, Downloaded from http://circep.ahajournals.org at Thomas Jefferson University on Jul. 27, 2015, 12 pages.

Joseph A. Potkay, Long term, implantable blood pressure monitoring systems, Biomed Microdevices (2008) 10:379-392, DOI 10.1007/s10544-007-9146-3, Published online: Dec. 20, 2007, 14 pages.

Wolf W. Von Maltzahn, Medical Instruments and Devices VIII, University of Texas at Arlington, Copyright 2000, 235 pages.

MEMS Pressure Sensor Solutions, Amphenol Advanced Sensors, NOVA Sensor, AAS-BR-212C-05/2015, 8 pages.

A. Vasudev et al., Microelectromechanical systems (MEMS) for in vivo applications, DOI: 10.1533/9780857096289.3.331, Copyright 2013,13 pages.

Pinet E. et al., Miniature Fiber Optic Pressure Sensor for Medical Applications: an Opportunity for Intra-Aortic Balloon Pumping (IABP) therapy, Abstract, downloaded from: http://proceedings.spiedigitallibrary.org/ on Jun. 18, 2014, 4 pages.

U.S. Department of Health and Human Services, Prevention, Detection, Evaluation, and Treatment of High Blood Pressure, National Institutes of Health, National Heart, Lung, and Blood Institute, NIH Publication No. 04-5230, Aug. 2004, 104 pages.

ISA, Remote Vital Signs Monitoring, Project Report Version 1.0, Emeline Alves Goncalves—Nr. 501022516, Sep. 10, 2007, Physics Department, Faculty of Sciences and Technology, University of Coimbra, 104 pages.

David M. Cutler et al., The Value of Antihypertensive Drugs: A Perspective on Medical Innovation, Health Affairs—vol. 26, No. 1, (2007): 97-110, DOI 10.1377/hlthaff.26.1.97, Downloaded from content.healthaffairs.org by Health Affairs on Jul. 10, 2014 at Thomas Jefferson University, 15 pages.

Baozhi Chen & Dario Pompili, Transmission of Patient Vital Signs Using Wireless Body Area Networks, Mobile Netw Appl, DOI 10.1007/s11036-010-0253-7, Published online: Jul. 6, 2010,20 pages.

Armand Pruijmboom et al., VCSEL-based miniature laser-Doppler interferometer, Proc. of SPIE vol. 6908 690801-1, 7 pages.

\* cited by examiner

IMPLANTABLE VITAL SIGN SENSOR

CROSS-REFERENCE TO RELATED APPLICATION

This application is related to and claims priority to U.S. Provisional Patent Application Ser. No. 62/143,592, filed Apr. 6, 2015, entitled "IMPLANTABLE VITAL SIGN SENSOR", and is also related to and claims priority to U.S. Provisional Patent Application Ser. No. 62/168,754, filed May 30, 2015, entitled "IMPLANTABLE VITAL SIGN SENSOR", the entire contents of both of which are hereby incorporated herein by reference.

STATEMENT REGARDING FEDERALLY SPONSORED RESEARCH OR DEVELOPMENT n/a

FIELD

An implantable vital signs sensor and method of implantation thereof.

BACKGROUND

Real-time monitoring of a non-ambulatory patient's vital signs is typically achieved through non-invasive methods. For example, a patient in an operating room or ICU bed may have a blood pressure monitor with a cuff disposable about the upper arm; a pulse oximeter engaged around a fingertip; adhesive electrodes affixed to the skin (proximate to the heart) that measure the electrocardiogram and respiratory rate/pattern of respiration; an oral/aural thermometer that measures body temperature, and a stethoscope for monitoring heart/lung/airway sounds. These non-invasive vital signs sensors are often cumbersome and unwieldy. Patients that are hospitalized, immobilized, or stationary commonly tolerate the inconveniences inherent in non-invasive sensors.

The real-time monitoring of an ambulatory patient's vital signs, however, is more challenging owing to the patient's mobility, and lack of supervision by hospital staff. Many patients are not compliant obtaining frequent or timely vital sign measurement using non-invasive sensors. Moreover, even when a patient is attentive to compliance, the cumbersome nature of such devices often results in patient's either removing the devices or shifting the devices to a more comfortable position, which can create artifacts, inaccurate readings, and occlude blood flow. Moreover, non-invasive devices are typically less accurate and less stable than implantable sensors.

Long-term implantable intravascular blood pressure sensors have been devised to measure blood pressure in real-time. However, such intravascular blood pressure sensors are prone to obstruct blood flow and cause endothelial cell injury, thrombosis, and emboli. Other long-term implantable blood pressure sensors are disposed around the outer diameter of an artery wall and use application to produce a robust mechanical coupling with the transducer's diaphragm. Still other implantable blood pressure sensors are used for short periods of time in the operating rooms, catheterization laboratories, and ICUs of a hospital.

SUMMARY

An implantable vital signs measurement device for a patient having an artery with an arterial wall, the arterial wall having a basement membrane, the device comprising an elongate and biodegradable housing including a first portion, the first portion defining a first open end, a second open end opposite the first end, and a lumen there through, the first portion being sized to be implanted substantially entirely within the arterial wall of the patient and having a length between 100-1500 microns, and a second portion substantially orthogonal with the first portion and configured to contour an exterior surface of the arterial wall when the distal end of the first portion is inserted to a position within the arterial wall substantially co-planar to the basement membrane and endothelial cells of the arterial wall. A sensor module having a proximal portion and a distal portion is included, the distal portion being insertable within the lumen and the sensor module being retainable within the first portion; at least a portion of the proximal portion is configured to seal the first open end and to provide for a predetermined insertion depth when distal portion of the sensor module is inserted within the lumen, the proximal portion being further configured to be pressed against the second portion of the housing when the distal portion of the sensor module is inserted within the lumen. The sensor module having a pressure transducer configured to measure an arterial blood pressure waveform, the sensor module having a delectable diaphragm responsive to a blood pressure waveform within the artery, the diaphragm being substantially co-planar to the basement membrane and endothelial cells of the arterial wall when the sensor module is retained within the first portion. A sensor module retaining element coupled to the sensor module is included, the sensor module retaining element configured to retain the sensor module within the first portion.

BRIEF DESCRIPTION OF THE DRAWINGS

A more complete understanding of the present invention, and the attendant advantages and features thereof, may be more readily understood by reference to the following detailed description when considered in conjunction with the accompanying drawings wherein.

DETAILED DESCRIPTION

Figure 1:
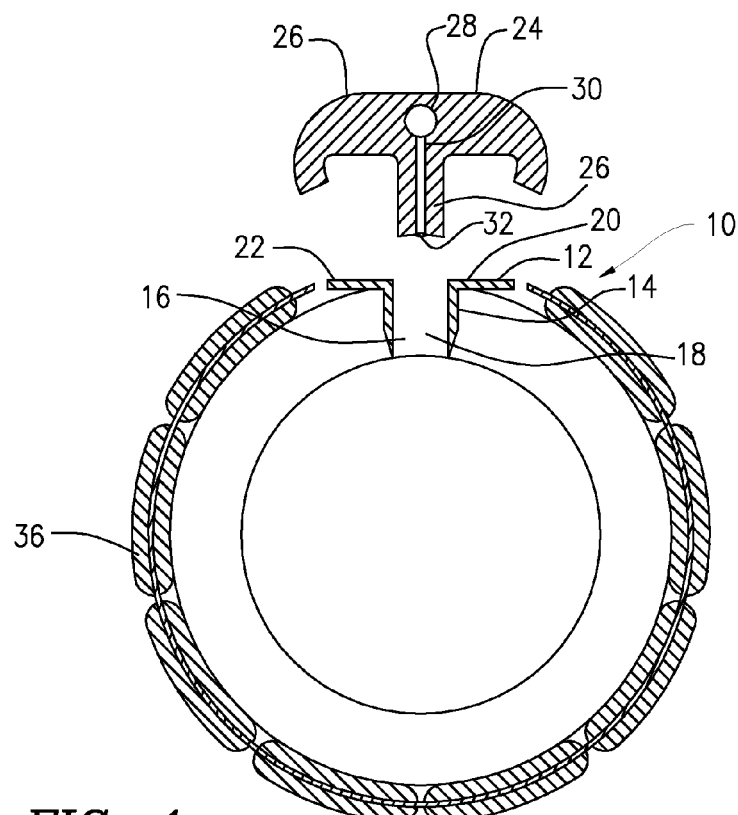
FIG. 1 is a front cross-sectional view of an embodiment of implantable sensor constructed in accordance with the principles of the present invention.

As used herein, relational terms, such as "first" and "second," "over" and "under," "front" and "rear," "in, within, and around" and the like, may be used solely to distinguish one entity or element from another entity or element without necessarily requiring or implying any physical or logical relationship or order between such entities or elements.

Referring now to the drawings in which like reference designators refer to like elements, there is shown in FIGS. 1-5 an exemplary implantable vital signs sensor device and monitoring system constructed in accordance with the principles of the present application and designated generally as "10." As used herein the phrase "vital signs" refers to measurements related to a patient's, whether human or animal, basic body functions, including but not limited to, heart rate, blood pressure, blood pressure waveform, blood flow, respiratory rate, tidal volume, electrocardiogram, temperature, hemoglobin oxygen saturation, body position, activity level, and related measurements. The device 10 may include a housing 12 sized to be at least substantially retained entirely within a blood vessel wall of a patient, and in particular, the wall of a vein or an artery.

The long-term implantable vital sign monitoring device 10 may monitor one or more of the following parameters in real-time to determine a significant change from an individual patient's baseline pattern when living in the real-world environment: heart rate, heart rhythm, stroke volume, blood pressure, systemic vascular resistance, blood flow, myocardial contractility, valve function, cardiac timing intervals, respiratory rate, respiratory rhythm, tidal volume, hemoglobin oxygen saturation, heart sounds, lung sounds, upper airway sounds, bowel sounds, temperature, electrocardiogram (lead 2, V2, and V5), activity level, body position, and location on the earth. The long-term implantable vital sign monitoring device 10 may also record one or more of the parameters for subsequent interpretation.

For example, the housing 12 may be sized to span the wall thickness of at least one of the internal thoracic (mammary) arterylateral thoracic artery, subscapular artery, intercostal artery, superior epigastric artery, carotid artery, aorta, renal artery, iliac artery, femoral artery, brachial artery, ulnar artery, and radial artery, which may range in wall thickness between approximately 100-1500 microns. For example, the housing 12 may be sized to span the wall thickness of at least one of the internal thoracic vein, lateral thoracic vein, jugular vein, vena cava, axillary vein, brachial vein, iliac vein, femoral vein and a peripheral vein, which may range in wall thickness between approximately 40-1000 microns. In addition, the housing 12 may be sized to span the wall thickness of a pulmonary artery or a pulmonary vein, which may range in wall thickness between approximately 40-1000 microns. The housing 12 may be composed of biodegradable and biocompatible materials, such that it may degrade after a predetermined amount of time within the body. Alternatively, the housing 12 may be composed of a biocompatible material such as stainless steel, titanium, composite, ceramic, silicone, PTFE, PE, PVC, epoxy, or glass that does not degrade over time. The housing 12 may be smooth or textured and coated with one or more compounds that promote the adhesion and health of the vessel wall tissue.

The housing 12 may include a first portion 14 sized to substantially span the entirety of wall thickness of the artery or vein into which the housing 12 is implanted. The first portion 14 may be substantially cylindrical in shape and define a lumen 16 there through. For example, when inserted within the internal thoracic artery, the first portion 14 may define a length of approximately between 300-600 microns and a surface area of approximately 1 mm². In other configurations, the first portion 14 may define any hollow structure sized to substantially span the arterial wall thickness and provide the lumen 16 there through. The first portion 14 may further define a smooth outer surface to facilitate placement within the artery wall tissue, or alternately, may be threaded on its outer surface such that the first portion 14 may be secured within the artery wall tissue through rotation of the first portion 14. The first portion 14 may be adhered within the arterial wall with an adhesive, or alternatively, may include a textured surface, barbs or tines that engage the surrounding tissue. The first portion 14 further includes an open first end 18 configured to be positioned immediately adjacent to the basement membrane and endothelial cells of the artery (tunica intima) such that the first open end 18 is not in contact with blood flowing within the artery or vein and a second open end 20 opposite the first end 18. In an exemplary configuration, the distance between the first open end 18 and the blood stream when the first portion 14 is implanted within the arterial wall may be approximately 5 to 200 microns. In another configuration, the first open end 18 is substantially co-planar with the basement membrane and endothelial cells. In another configuration, the first end can extend 5 to 200 micrometers into the artery lumen, in contact with the flowing blood.

Attached to the second end 20 may be a second portion 22 of the housing 12. The second portion 22 may be positioned substantially orthogonal to the first portion 14 and may extend across and contour at least a portion of the outer diameter of the arterial wall. For example, the second portion 22 may be substantially flat, rectangular, or round in shape, or alternatively, may define a curvature substantially corresponding to the curvature of the outer diameter of the arterial wall such that when the first portion 14 is received within the arterial wall, the second portion 22 may be pressed against the outer diameter of the arterial wall. The second portion 22 may further define a flat interior surface and a rounded or bulbous exterior surface such that the second portion 22 protrudes a distance away from the outer diameter of the artery. The distance between the first end 18 and interior surface of the second portion 22 may be prefabricated such that when the second portion 22 is pressed against the arterial wall, the first end 18 is position immediately adjacent to the basement membrane and endothelial cells. Thus, the second portion 22 is configured to operate as a stopper to facilitate the insertion of the first portion 14 to the desired depth within the arterial wall.

Ultrasound may be used to measure the artery wall outer diameter, wall thickness, and inner diameter to determine the appropriate length/size of the housing 12, the first portion 14, and the second portion 22. In particular, the surgeon may select from pre-fabricated bases with a particular height of the first portion 14 and length of the second portion 22 to accommodate differently sized arteries or veins within the same patient or different wall thickness between different patients.

A vital signs sensor module 24 may be releasably or permanently inserted and received within at least a portion of the housing 12. For example, at least a portion of the vital signs sensor module 24 may be inserted through the second open end 20 into the lumen 16 of the housing 12. The module 24 may include a sensor housing 26 that includes one or more biosensors, such as a force or pressure transducer, configured to measure one or more physiological parameters of the patient, which can be transduced and correlated into one or more vital sign measurements. In particular, the sensor module 24 may include a pressure transducer configured to correlate a measured deflection of a diaphragm disposed within to a blood pressure measurement, as discussed in more detail below. The module 24 may be slideably received within the lumen 16 such that it is retained within the lumen 16 and within the arterial wall. In one configuration, the module 24 includes a capillary tube 28 with an optical fiber 30 or optical sensing mechanism 30, with a transducer diaphragm 32 on its distal tip. For example, the capillary tube 28 may have an optical fiber or optical sensing mechanism 30 disposed within the tube 28 having a rigid, semi-flexible, or flexible diaphragm 32 at its distal end, a portion of which is received within the lumen 16 and positioned to about the tunica intima cells of the artery proximate the first open end 18.

Figure 2:
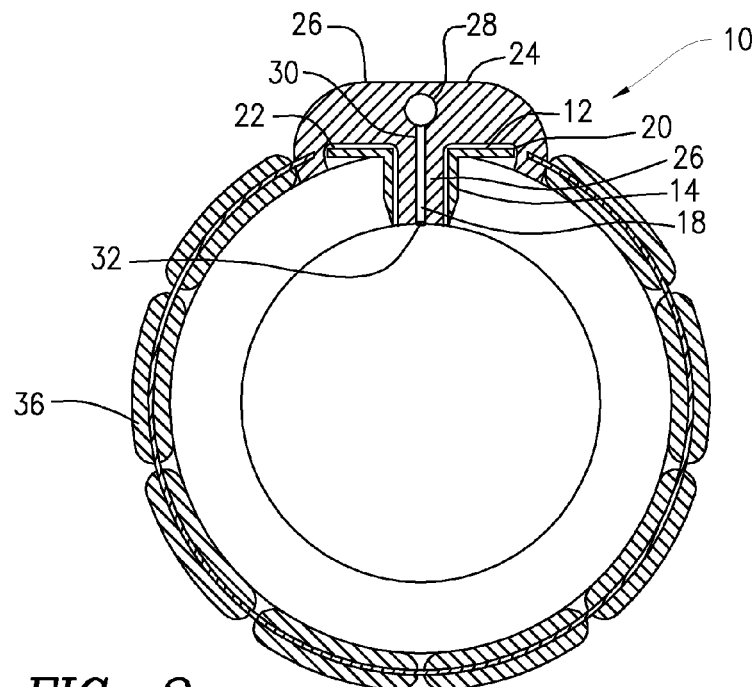
FIG. 2 is a front cross-sectional view of the implantable sensor shown in FIG. 1 implanted within a blood vessel wall.

As shown in FIG. 1-2, the optical fiber 30 extends through the housing 26 and extends outward from the artery in a position substantially parallel to the length of the artery, but may extend in any direction. In one embodiment, the optical fiber 30 is not required and an optical sensing mechanism may be included as part of the module 24 to measure the displacement of the diaphragm 32 with each pulse to measure the blood pressure (BP) waveform. Each pulse through the artery or vein may cause the tissue and diaphragm 32 to move inward/outward a distance proportional to the energy of the pulse wave, which may be correlated to produce a measurement of the BP waveform. In an exemplary configuration, the diaphragm 32 is covered only by the endothelial cells, basement membrane, and/or a small amount of connective tissue. In one configuration, embodiment has the optics and electronics housed within the sensor housing 26 and the capillary tube 28 and the diaphragm 32 housed within lumen 16. Once implanted in the body, the basement membrane and endothelial cells may grow from the edges of the injured artery wall tissue, over the surface of the diaphragm 32 to produce a continuous biocompatible/hemocompatible interface. The very thin layer of cells and/or connective tissue that may cover the outer surface of the diaphragm 32 may stabilize, and not affect, the measurement of the intravascular blood pressure waveform.

Examples of pressure transducers that may be included in the sensor module 24 include those with single or multiple deflectable diaphragms 32 with a Wheatstone bridge configuration, a single or multiple piezoelectric crystal configuration, or an optical configuration that accurately measures diaphragm 32 motion. Because the diaphragm 32 is positioned against the tunica intima, the module 24 may produce an accurate measurement of the intravascular blood pressure waveform without distortion and without compressing or flattening of the artery wall, the artery lumen, the vein wall, or the vein lumen.

After implantation, the outer surface of the diaphragm 32 may remain clean or become coated with protein, carbohydrate, lipid and other compounds. The outer surface of the diaphragm 32 can also become coated with basement membrane, other connective tissue and endothelial cells. The surface of the diaphragm 32 may be textured or coated with a natural or synthetic biomaterial to enhance the adhesion of basement membrane and endothelial cells (tunica intima). Coating the outer surface of the diaphragm 32 may change the physical characteristics of diaphragm 32 motion. This coating layer (not shown) may become stable within days to weeks of implantation in the body. Thus, the implanted pressure/force sensor remains stable over time and may require infrequent re-calibration using an external BP cuff measurement system as a reference. The reference BP cuff may also contain a barometer and thermometer (measures atmospheric pressure and temperature) to enhance calibration of the implanted BP sensor.

In other configurations, the transducer's diaphragm 32 may be positioned exterior to the arterial wall, any depth within the arterial wall, or within the artery lumen exposed to flowing blood. For example, a post (not shown) may be located within the flowing blood (artery lumen) with a diaphragm 32 on its distal end or on the side of the post. The intravascular post may be inserted at a right angle to the inner wall of the artery (90 degrees) or any angle relative to the inner wall of the artery (+320 to 0 to −320 degrees). The module's 24 diaphragm 32 may be positioned on the side of the post toward the flow of blood and any position relative to the flow of blood, (0 to 360 degrees). The intravascular post BP sensor module 24 can also be re-calibrated using a reference upper arm BP cuff. An external barometer and thermometer may be used to measure changes in atmospheric pressure and temperature to enhance calibration accuracy of the implanted BP sensor's output signal.

The module 24 may further be configured to measure a patient's blood pressure waveform in real-time. The waveform can be analyzed to determine: heart rate, heart rate variability, stroke volume, stroke volume variability, myocardial contractility, vascular resistance, systolic and diastolic timing interval, aortic and mitral valve function, blood flow, and respiratory rate/pattern of ventilation. For example, the sensor modules 24 may include a processor configured to correlate the measured physiological parameters into a vital signs measurement that can be transmitted and/or stored with a memory. The module 24 may further include one or more additional vital signs sensors disposed within the housing 26 or disposed along or within other portions of the module 24. For example, a hemoglobin oxygen saturation sensor, temperature sensor, an ECG electrode, an acoustic sensor, and an activity sensor may be included as part of the module 24, as discussed in more detail below.

The module 24 may include a sensor module retaining element 34 disposed around the circumference of the artery or vein. The sensor module retaining element 34 may include a plurality of links 36, each link 36 being movably connected to an adjacent link 36 to define a partial perimeter around the artery or vein. The plurality of links 36 may connect to the sensor housing 26 or the second portion 22 to completely surround the artery or vein. The movability of the links 36 allows for the artery to pulse as blood flows through it without constricting the artery or vein and maintaining contact of the housing 26 with the arterial or venous wall. The mechanism holding the links to each other the sensor module and the blood vessel wall may have a small, moderate, or large degree of elasticity. The inner surface of each link 36 may further define a porous/textured surface such that it may fuse with the arterial or venous wall tissue such that the arterial or venous wall and the links 36 may move substantially simultaneously during pulsatile blood flow. The links may also have one or more through and through openings or channels that permit the ingrowth of vessel wall tissue and vaso-vasorum. A hemoglobin oxygen saturation sensor (pulse oximeter-SpO$_2$) 38 may be integrated within the body of one or more links or the housing 26. For example, in a configuration with five links 36 disposed around the circumference of the, a component of the SpO$_2$ sensors 38 may be affixed within one or more links 36 to provide for a plurality of photoplethysmograph waveforms and SpO$_2$ measurements. In one configuration, each link 36 has a recess (not shown) sized to receive one of the SpO$_2$ sensor components, for example, the light source and/or detector such that the only barrier between the blood flow within the artery and the SpO$_2$ sensor 38 is the arterial wall tissue. The pulse oximeter light source and light detector may be located on the same link or separate links located on opposite sides of the artery. Each SpO$_2$ sensor 38 may be in communication with the processor inside the housing 28, for example, by a conductor disposed within the sensor module retaining element 34 connecting each SpO$_2$ sensor to each other and to the processor. Optionally, other sensors, for example, an ECG sensor or other electrodes may be disposed within or around the sensor module retaining element 34. For example, electrodes may be disposed on opposite sides of the sensor module retaining element 34 to measure the electrocardiogram, volume of blood flow, rate of blood flow, temperature, heart/lung sounds, respiratory rate, and pattern of ventilation.

Figure 3B:
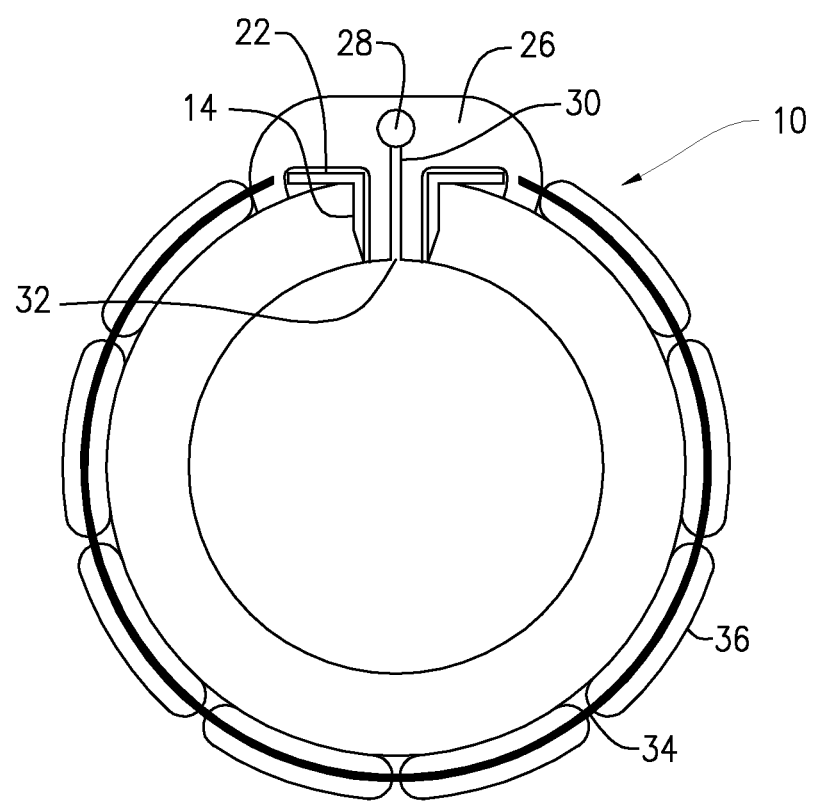
FIG. 3B is a front cross-sectional view of the implantable sensor shown in FIG. 3A.
Figure 4:
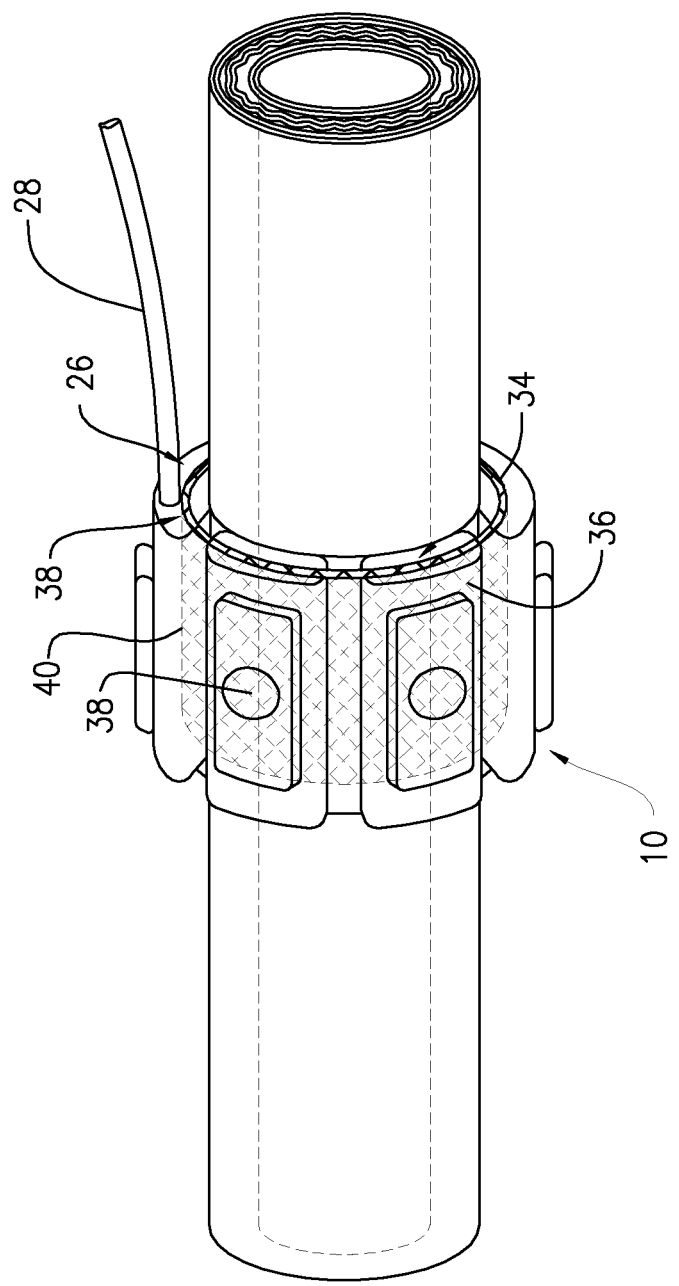
FIG. 4 is a front cross-sectional view of the implantable sensor shown in FIG. 1 with an outer flexible stent or fabric that holds the sensor against the blood vessel wall and within the blood vessel wall tissue.

Now referring to FIG. 4, in other configurations, the sensor housing 26 may be secured to the outside wall of the artery with a flexible and elastic stent, fabric, or mesh 40 disposed within a portion of the links 36. These materials may have an open structure to decrease mass and facilitate the ingrowth of tunica adventicia and vasa vasorum. For example, the sensor housing 26 may be fabricated with a flexible stent 40 sized to be disposed around the circumference of the artery to affix the capillary tube 28 and transducer diaphragm 32 within the lumen 16. The stent, fabric, or mesh 40 may be non-biodegradable such that it may not degrade overtime, or alternatively, may be biodegradable such that over a predetermined amount of time the stent, fabric, or mesh 40 may degrade leaving the module 24 affixed to the tunica adventicia tissue and the capillary tube 28 affixed to the artery wall tissue. The stent, fabric, or mesh may define a larger diameter to that of the module 24 to surround the module 24 and stents 40. Surgical clips, sutures, or a tissue adhesive are further contemplated to be used to secure the module 24 to the artery wall tissue in combination with the stent 40 or as an alternative. For example, as shown in FIG. 3B, sutures are thread through a portion of each link 36 and attach directly to the module 24. Each link 36 may define one or more apertures or channels through with the sutures, belts, or stents 40 may be disposed to facilitate the securing the housing 26 to the arterial wall.

Figure 5:
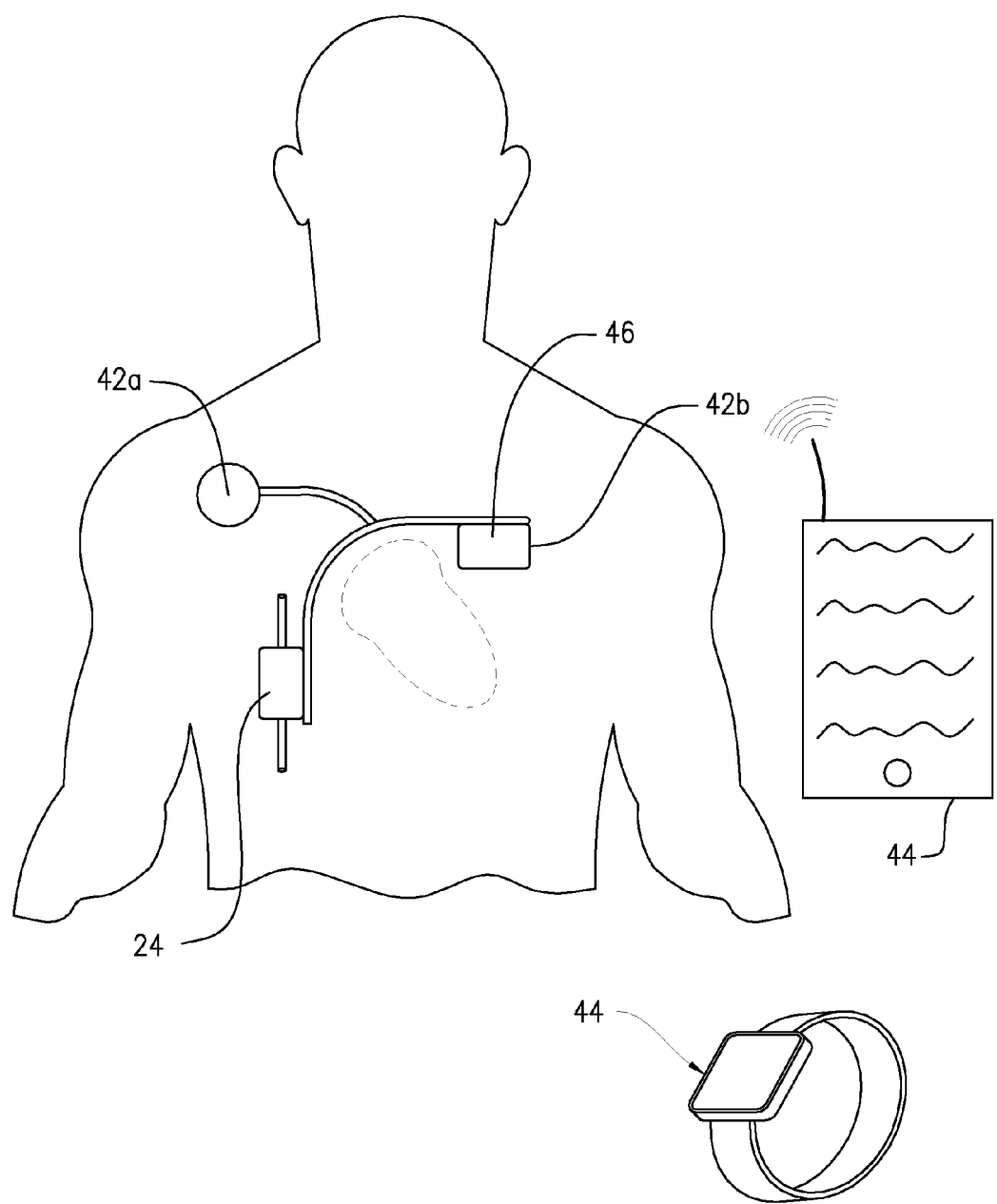
FIG. 5 is a system view of exemplary implanted vital signs sensors in communication with a watch and tablet computer.

Referring now to FIG. 5 which illustrates the location of sensor module 24 implanted around the right internal mammary artery and an additional sensor module 42a implanted within the subcutaneous tissue of the right upper chest wall, and a second additional sensor module 42b implanted within the subcutaneous tissue of the left upper chest wall. Each sensor module 24, 42a, and 42b, can be constructed with one or multiple vital sign sensors per module. For example, subcutaneous tissue sensor modules 42a and 42b may include an EKG electrode, a microphone, a GPS sensor, an accelerometer, and a temperature sensor. The implanted sensors 24, 42a, and 42b may communicate with an external controller 44 with a display through radiofrequency telemetry. For example, the controller may be a Smartphone, tablet device, or smart watch, such as an iPhone®, iPad®, Apple Watch® 44 (FIG. 5), or FitBit®, with an application in communication with a processor having processing circuitry configured to communicate with the implanted sensors 24, 42a, and 42b and display the measured information. In one configuration, the user may wear a smart watch with built-in wireless communication to communication with the implanted sensors 24, 42a, and 42b, correlate the measured data, and display the results. The controller 44 may be used by the patient and physician to display and processes the real-time and recorded sensor data, calibrate the sensors, and troubleshoot the sensors. The controller 44 may contain a barometer that measures the real-time atmospheric pressure to produce a calibrated and accurate absolute blood pressure measurement. The controller 44 may contain a thermometer that measures the real-time atmospheric temperature to produce a calibrated and accurate absolute blood pressure measurement.

The implanted sensors 24, 42a, and 42b can be in communication with a charge storing device (battery) 46 implanted within the body separate from the sensors 24, 42a, and 42b or within the sensor module 24, 42a, or 42b. The charge storing device 46 may be a hermetically sealed battery implanted within the body in wired communication with the implanted sensors 24, 42a, and 42b. The implantable battery 46 may be re-charged across the skin using an external power source by, for example, inductive charging. In an alternate embodiment, the energy for the implanted sensors 24, 42a, and 42b to function may be transmitted from the outside of the body through the skin and the subcutaneous tissue using electromagnetic coupling or light coupling. Transmission of external power to the internal sensors 24, 42a, and 42b requires low energy and thus a short transmission distance. The external power source may be located near or adhered to the skin surface for extended periods of time to power the implanted vital sign monitoring device or recharge the implanted battery.

The module 24 containing the blood pressure sensor may be implanted around the internal thoracic (mammary) artery (between the $3^{rd}$-$4^{th}$, $4^{th}$-$5^{th}$ or $5^{th}$-$6^{th}$ intercostal space) using local or general anesthesia. That artery is located perpendicular to the ribs, approximately 1 cm lateral to the sternum, and between the inner and middle intercostal muscles. In an exemplary configuration, the module 24 may be implanted at the level of the aortic valve to minimize the effects of body position on the arterial pressure waveform and the absolute blood pressure measurement. In an exemplary method of implantation, the surgeon may use a small needle, punch or an automated stapling device to puncture the wall of the artery or vein. In part because the needle may create a tapered opening in the arterial wall, the first portion 14 of the housing 12 may be inserted within the aperture created by the needle such that the first open end 18 is substantially planar or partially recessed from the basement membrane and endothelial cells. In other configurations, the needle may pierce entirely through the wall of the blood vessel. The lumen 16 of the housing 12 may be slid around the circumference of the needle and affixed inside the aperture with the artery wall tissue. The capillary tube 28 of the module 24 may then be inserted within the lumen 16 of the housing 12 for affixation within the housing 12 such that one or more transducer diaphragms 32 may be positioned substantially coplanar with the opening of the first end 18. The stents 40 may be positioned around the outside of the artery or vein and attached to the sides of the module 24 to secure the housing 12 within the artery wall tissue and the module 24 to the outside of the blood vessel wall.

Figure 3A:
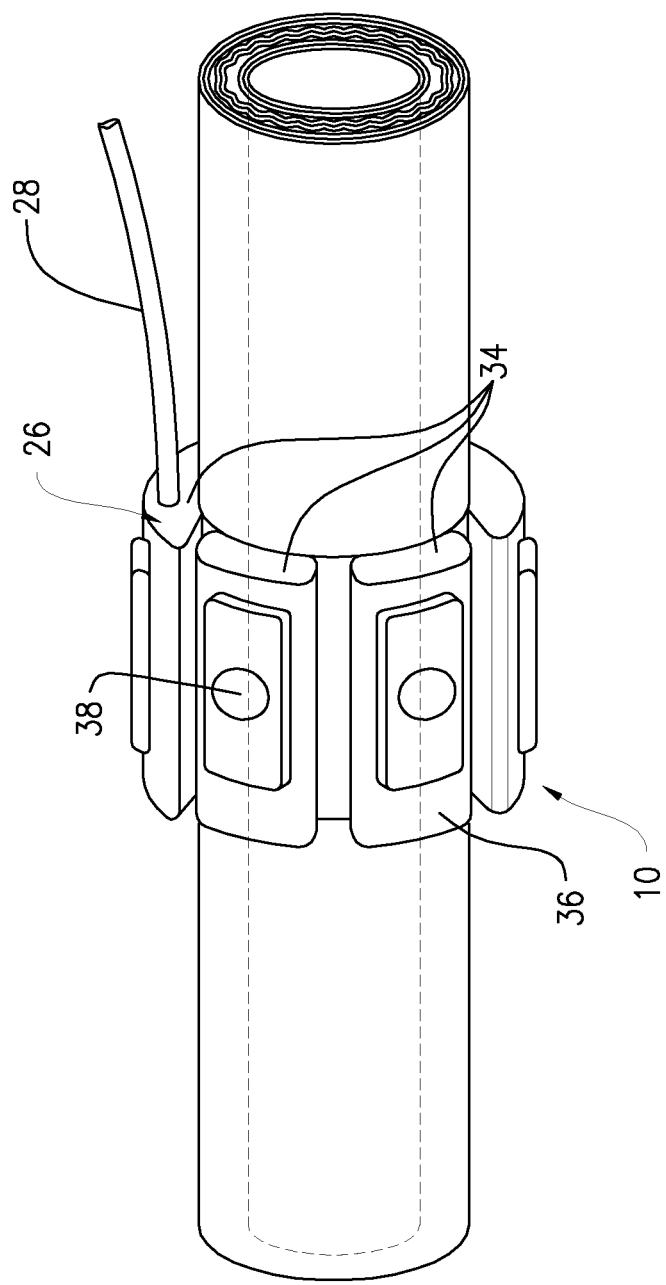
FIG. 3A is a side view of the implantable sensor shown in FIG. 2.

In an exemplary configuration of the module 24, as shown in FIG. 3, two or more blood pressure sensor waveform transducers can be positioned around the artery with the transducer's diaphragm 32 immediately adjacent to the endothelial cells. The $SpO_2$ sensor 38 may be configured with one or more light sources and light detectors external to the artery wall (tunica adventicia); opposite one another (12 o'clock and 6 o'clock positions). This alignment may produce a real-time photoplethysmography signal with a high signal-to-noise ratio and minimal motion artifact. The $SpO_2$ sensor's 38 light sources and detectors may also be located within the artery wall tissue adjacent to the endothelial cells. The external surface of the module 24 (containing the BP sensor and $SpO_2$ sensor), the stents 40, and the additional sensor modules 42a and 42b may have a metal conducting surface, for example, an electrode that can measure the real-time electrocardiogram signal of the heart (ECG or EKG) and the electrical signals due to movement of the diaphragm and chest wall. The module 24 and additional sensor modules 42a and 42b may also contain a temperature thermistor that continuously measures the core or blood temperature and one or more microphones that monitor and record the heart sounds (phonocardiogram), lung sounds, upper airway sounds, and gastrointestinal sounds.

The measured vital signs from module 24 and/or implanted sensors 42a and 42b may be used to alert, diagnose, and/or treat associated diseases or conditions that can be correlated from the measured vital signs. For example, measurements taken from one or more of the implanted sensors, namely, ECG, blood pressure, pulse oximeter, thermometer, microphone, accelerometer, GPS may be combined and processed in real-time to provide diagnostic and/or therapeutic recommendations and/or therapies to the patient. Trend data from the implanted sensors can be combined with trend data from non-invasive sensors, for example, a scale measuring body weight and a camera capturing an image of a patient's head, neck, and torso, to provide diagnostic and/or therapeutic recommendations and/or therapies to the patient.

In an exemplary configuration, the one or more measured vital signs may be monitored in an ambulatory patient and displayed and/or stored on the controller 44 or a remote database, for example, to a physician's office and/or a central monitoring station with real-time diagnostic algorithms and a detailed patient electronic medical record (EMR). The measured vital signs may then be compared against a threshold value predetermined by the patient's physician or an algorithm based on the patient's baseline vital sign information. For example, based on the user's weight, height, age, family history, medications, and medical history, and prior vital signs data, the algorithm may determine a threshold value or range for one or more of the vital sign measurements that the processor in the controller 44 or a remote location, may compare against each other to determine if a medical condition exists and alert the patient, for example, via a call, text, or alarm to the controller 44, a third-party Smartphone, or an email that summarizes the condition. The algorithm may trigger an event to record important vital sign sensor data and transmit the trend data to the external control module and central monitoring station for review and clinical analysis. Ambulatory patients may receive audible or visual alerts and alarms when the vital sign sensor algorithms detect a significant change in vital sign trend data. The patient may manually enter a diary of symptoms, signs, meals, medications into the diagnostic/therapeutic software algorithms to manage their disease with greater safety and efficacy. Clinicians at a central monitoring system can communicate with the patient via cell phone to initiate/adjust medical therapy and summarize the effects of that therapy over time. Described below are several diagnostic algorithms that may use multi-modal monitoring (trend data from more than one vital sign sensor) to diagnose the following conditions:

Myocardial Ischemia and Myocardial Infarction—real-time monitoring of the ECG can be used to diagnose myocardial infarction and ischemia by analyzing ST segment depression (horizontal or down-sloping) or elevation in relation to heart rate, BP, & activity level; new onset Q waves; unifocal and multifocal premature ventricular contractions; premature atrial contractions; supraventricular tachycardia, atrial fibrillation, new conduction delays, and new heart block related to myocardial ischemia, myocardial infarction and heart failure. Real-time monitoring of the blood pressure waveform can detect changes in BP, heart rate, stroke volume, myocardial contractility, systemic vascular resistance, cardiac output, systolic/diastolic timing intervals, valve function, and respiratory rate that typically occur with myocardial ischemia at rest and with exercise. Real-time monitoring of cardiac sounds can detect wheezing, rhales, S-3 sound, and a new murmur of mitral/aortic valve regurgitation due to myocardial ischemia, LV dysfunction, and pulmonary edema. Real-time monitoring with a pulse oximeter may detect an acute decrease in the arterial hemoglobin oxygen saturation that may occur with myocardial ischemia at rest and with exercise. Changing from a stable to an unstable pattern would be considered a medical emergency requiring increased vigilance and optimized/timely medical therapy.

Congestive Heart Failure and Pulmonary Edema—Real-time monitoring of the blood pressure waveform may be used to detect changes in myocardial contractility, stroke volume, stroke volume variability, heart rate, heart rate variability, systolic/diastolic timing intervals, valve function and respiratory rate that may occur with myocardial ischemia, infarction, cardiomyopathy and heart failure. Real-time monitoring of cardiac & lung sounds can detect wheezing, rhales, S-3 sound, and a new murmurs due to LV dysfunction and acute pulmonary edema. Real-time monitoring with a pulse oximeter may detect an acute decrease in the arterial hemoglobin oxygen saturation. Changing from a stable to an unstable pattern would be considered a medical emergency requiring increased vigilance and optimized/timely medical therapy.

Hypertension (Mild, Moderate & Severe) real-time monitoring of the blood pressure waveform pattern may be used to diagnose hypertension (mean, systolic & diastolic BP>target range for age) and determine the effectiveness of medical/drug/device therapy. For example, a sustained upward trend for systolic, diastolic, and mean blood pressure and/or persistent tachycardia in relation to activity, rest, and sleep may require a change in medication. Medication dose may be adjusted to real-time BP data and trend data. Monitoring the ECG can detect the acute and chronic effects of hypertension on left ventricle wall thickness and myocardial electrical activity (LV hypertrophy with strain pattern). New onset moderate/severe hypertension or changing to an unstable BP pattern would be considered a medical emergency requiring increased vigilance and optimized/timely medical therapy.

Atrial Fibrillation or Supraventricular Tachycardia—real-time monitoring of the ECG can diagnosis new onset or recurrent atrial fibrillation and/or supraventricular tachycardia that occurs spontaneously or secondary to myocardial ischemia, CHF, or hypertension. Real-time monitoring of the arterial BP waveform can detect the hemodynamic significant of an arrhythmia (decreased BP, stroke volume, and cardiac output). Monitoring the pulse oximeter during the arrhythmia can detect decreased hemoglobin oxygen saturation due to decreased and unstable blood flow. New onset atrial fibrillation, SVT or changing to an unstable rhythm pattern would be considered a medical emergency requiring increased vigilance and optimized/timely medical therapy.

Acute Bronchospasm (Asthma)—Changes in the vital signs measurements may be used to diagnose upper airway obstruction, large airway obstruction and bronchospasm (due to asthma or bronchitis) and pneumothorax. Real-time monitoring of cardiac, lung, and upper airway sounds can detect wheezing, rhales, rhonchi, increased respiratory rate/tidal volume (minute ventilation) and prolonged exhalation (increased work of breathing). Monitoring the arterial BP waveform can detect increased heart rate, increased heart rate variability, decreased stroke volume, increased stroke volume variability, and decreased cardiac output. Monitoring the ECG can detect an increased HR, decreased HR variability, arrhythmias, and acute right ventricle strain. Monitoring the pulse oximeter can detect an acute decrease in hemoglobin oxygen saturation. New onset bronchospasm with a high work of breathing and decreased hemoglobin oxygen saturation would be considered a medical emergency requiring increased vigilance and optimized/timely medical therapy.

Chronic Obstructive Pulmonary Disease & Respiratory Failure—Changes in the vital signs measurements may be used to diagnose acute respiratory failure and a worsening of chronic bronchitis and emphysema due to acute bronchitis or pneumonia. For example, an increase in respiratory rate and minute ventilation, coughing, wheezing, decreased hemoglobin oxygen saturation, persistent tachycardia, myocardial ischemia, right heart strain, and elevated temperature may be indicative of such a condition. A persistently high work of breathing and decreased hemoglobin oxygen saturation would be considered a medical emergency requiring increased vigilance and optimized/timely medical therapy.

Intestinal Diseases (Chron's Disease, Ulcerative Colitis, Diverticulitis, Ischemia)—Changes in the vital signs measurements may be used to diagnose decompensation of inflammatory bowel disease. For example, increased/decreased bowel sounds (motility), elevated temperature, tachycardia, hypotension, decreased blood flow, tachypnea, decreased hemoglobin oxygen saturation may all be indicated of such a condition.

Pulmonary Embolism—Changes in the vital signs measurements may be used to diagnose a pulmonary embolism. For example, acute onset wheezing, increased respiratory rate, increased minute ventilation, tachycardia, atrial/ventricular arrhythmias, right ventricle strain pattern on EKG, decreased hemoglobin oxygen saturation, elevated temperature, decreased stroke volume, decreased cardiac output, and hypotension, may be indicated of such a condition. Any pulmonary embolism would be considered a medical emergency requiring increased vigilance and optimized/timely medical therapy.

Hemorrhage or Dehydration—Changes in the vital signs measurements may be used to diagnose significant dehydration due to bleeding, edema, decreased oral intake, excess urination, or diarrhea. For example, increase in heart rate, peripheral vascular resistance, respiratory rate, minute ventilation and a decrease in stroke volume, cardiac output, blood pressure, blood flow, and hemoglobin oxygen saturation, may be indicated of moderate to severe blood loss and/or dehydration.

The above conditions are merely exemplary of the number of ways the vital sign measurements determined from the sensor module 24 and/or additional sensor modules 42*a* and 42*b* may be measured and correlated in real-time against a patient established threshold to either signal an alert to the user, signal an alert to a medical professional (primary care physician or central monitoring station), or record the data for further evaluation. For example, a patient with known atrial fibrillation may have a different blood pressure threshold value compared to the blood pressure of a patient without atrial fibrillation. As such, the threshold value can be programmed by the doctor into the controller 44 or automatically by the remote database, such that when that threshold value is exceeded or falls below that threshold in a real-time ambulatory setting, depending on the threshold value, an alert may be sent to the patient, the central monitoring station, and/or the patient's physician. Similarly, patients with other conditions may have different thresholds for each vital sign measurement measured by the module 24 and/or 42 and 42*b* such that each module 24 in combination with the controller 44 may be personalized for each patient to provide an early warning sign of an individual condition prior to an adverse event. Alerts and alarms can be based upon a simple threshold, a predicted threshold, or based upon a model of the patient's physiology. Moreover, based on the vital signs measurements, a therapeutic algorithm may also be used in combination with the diagnostic algorithm to recommend and/or implement therapies for the patient based on the measured vital signs compared to the patient's individual threshold values or ranges. For example, the therapeutic algorithm may operate in the above conditions as follows:

Myocardial Ischemia—Physicians and patients currently titrate medications in response to symptoms such as "chest pain" (angina) despite the fact that greater than 80% of myocardial ischemia is silent and many "pains in the chest" are due to non-cardiac causes. Medications for ischemic heart disease may be dosed once or multiple times per day based upon quantitative vital sign data. Real-time data may be used to "recommend" an adjustment in medical therapy (nitrates, ACE inhibitors, beta blockers, calcium channel blockers, aspirin, anticoagulant, and oxygen) based on the patient's medical history and historical vital signs measurements. It is further contemplated that the real-time vital sign sensor system and closed-loop therapeutic algorithms may automatically deliver anti-ischemia medications using drug infusion pumps and/or oxygen using an oxygen source and regulator. Real-time data may also be used to automatically adjust electrical nerve tissue stimulation devices and cardiovascular blood pump devices that optimize blood pressure and blood flow in a sick heart.

Congestive Heart Failure & Pulmonary Edema—Changes in the patient's vital sign pattern may be used to detect the onset of CHF and pulmonary edema in the early stages as discussed above, such that management can occur in the ambulatory setting; avoiding a visit to the emergency room and admission to an intensive care unit. Real-time vital sign sensor data may be used to recommend an acute change in medical therapy (diuretics, catechamines, digitalis, nitrates, beta blockers, calcium channel blockers, ACE inhibitors, and oxygen). It is further contemplated that the real-time vital sign sensor system and closed-loop therapeutic algorithms may automatically deliver medications, oxygen, pacemaker therapy, ventricular assist device therapy, and total artificial heart therapy that may increase myocardial contractility, control HR, control BP, control blood flow, oxygen concentration, and decrease systemic vascular resistance using drug infusion pumps and electrical stimulation.

Hypertension—Real-time analysis of the BP waveform may calculate heart rate, heart rhythm, stroke volume, arterial blood flow, myocardial contractility, and systemic vascular resistance. Vital sign sensor data may be used to recommend an acute change in medical therapy (diuretics, beta blockers, alpha blockers, vasodilators, ACE inhibitors, calcium channel blockers) and monitor the effectiveness of that medical therapy. It is further contemplated that the real-time vital sign sensor system and closed-loop therapeutic algorithms may automatically deliver anti-hypertension medications using drug infusion pumps and electrical therapy of nervous tissue to maintain the mean, systolic, and diastolic BP is the target range during rest, exercise, sleep, and illness.

Arrhythmia—real-time vital sign sensor data may be used to recommend an acute change in medical therapy (beta blockers, calcium channel blockers, membrane stabilizers). It is further contemplated that real-time vital sign sensor system and closed-loop therapeutic algorithms may automatically deliver anti-arrhythmia medications using drug infusion pumps; and anti-arrhythmia electrical shock therapy using a defibrillation shock, a cardioversion shock and/or override pacemaker shocks.

Asthma—real-time vital sign sensor data may be used to recommend acute medical therapy (oxygen, catecholamine inhaler, steroid inhaler, parenteral catecholamines). It is further contemplated that the real-time vital sign sensor system and closed-loop therapeutic algorithms may automatically deliver anti-inflammatory and bronchodilator medications using drug infusion pumps, oxygen using an oxygen source/regulator, and electrical stimulation of nervous tissue to reduce bronchospasm and inflammation.

Chronic Obstructive Pulmonary Disease (COPD)—real-time vital sign sensor data may be used to recommend an acute change in medical therapy (oxygen, catecholamine inhaler, steroid inhaler, parenteral catecholamines). It is further contemplated that the real-time vital sign sensor system and closed-loop therapeutic algorithms may automatically deliver anti-inflammatory and bronchodilator medications using drug infusion pumps, oxygen using an oxygen source/regulator, and electrical stimulation of nervous tissue to reduce bronchospasm and inflammation.

Chronic Intestinal Diseases—real-time vital sign sensor data may be used to recommend an acute change in medical therapy (intravenous fluids, oxygen, steroids, anti-inflammatory). It is further contemplated that the real-time vital sign sensor system and closed-loop therapeutic algorithms may automatically deliver anti-inflammatory, pro-peristalsis, or anti-peristalsis medications using drug infusion pumps.

The measured vital signs data may further be processed to determine whether trend vital sign data is "abnormal" or "extreme" relative to a model of a universal healthy/stable patient or adapted to an individual patient. For example, hundreds to thousands of hours of patient vital sign data from any one or all of the sensors may be recorded and analyzed. Large data sets may be split into (1) training sets, (2) control sets, and (3) test sets. Clinical experts may review the trend data and label specific patterns as "crisis events" or "error codes." The algorithms may learn from an individual patient's physiological patterns and determine when the trend data is "abnormal" or "extreme" with high sensitivity and specificity (minimal false alerts/alarms and few missed "real" events). The real-time method may estimate the extreme value distributions of multivariate, multimodal mixture models for analysis of complex datasets from an array of physiological vital sign sensors.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An implantable vital signs measurement device for a patient having an artery with an arterial wall, the arterial wall having a basement membrane and endothelial cells, the device comprising:
    an elongate housing including:
        a first portion, the first portion defining a first open end, a second open end opposite the first end, and a lumen there through, the first portion being sized to be implanted substantially entirely within the arterial wall of the patient; and
        a second portion substantially orthogonal with the first portion and configured to contour an exterior surface of the arterial wall when the distal end of the first portion is inserted to a position within the arterial wall substantially co-planar to the basement membrane and endothelial cells of the arterial wall;
    a sensor module having a proximal portion and a distal portion, the distal portion being insertable within the lumen and the sensor module being retainable within the first portion; at least a portion of the proximal portion is configured to seal the first open end and to provide for a predetermined insertion depth when distal portion of the sensor module is inserted within the lumen, the proximal portion being further configured to be pressed against the second portion of the housing when the distal portion of the sensor module is inserted within the lumen;
    the sensor module having a pressure transducer configured to measure an arterial blood pressure waveform, the sensor module having a deflectable diaphragm responsive to a blood pressure waveform within the artery, the diaphragm being substantially co-planar to the basement membrane and endothelial cells of the arterial wall when the sensor module is retained within the first portion; and
    a sensor module retaining element coupled to the sensor module, the sensor module retaining element including a plurality of connected spaced apart links configured to surround the artery and to retain the sensor module within the first portion.

* * * * *